(12) United States Patent
Gonzalez et al.

(10) Patent No.: US 7,150,878 B2
(45) Date of Patent: *Dec. 19, 2006

(54) EXTENDED DURATION INSECT REPELLENT COMPOSITION AND METHOD OF APPLICATION TO THE SKIN

(75) Inventors: Anthony D. Gonzalez, Waldwick, NJ (US); Andrew H. Pechko, Ridgewood, NJ (US); Robert E. Kalafsky, Ogdensburg, NJ (US)

(73) Assignee: Avon Products, Inc., New York, NY (US)

( * ) Notice: Subject to any disclaimer, the term of this patent is extended or adjusted under 35 U.S.C. 154(b) by 139 days.

This patent is subject to a terminal disclaimer.

(21) Appl. No.: 10/203,839

(22) PCT Filed: Nov. 27, 2001

(86) PCT No.: PCT/US01/44299

§ 371 (c)(1),
(2), (4) Date: Aug. 14, 2002

(87) PCT Pub. No.: WO02/43491

PCT Pub. Date: Jun. 6, 2002

(65) Prior Publication Data

US 2003/0099679 A1    May 29, 2003

(51) Int. Cl.
*A01N 25/24* (2006.01)
*A01N 25/32* (2006.01)

(52) U.S. Cl. .................... 424/407; 424/59; 424/60; 424/401; 424/405; 424/406; 424/750; 424/757; 514/315; 514/514; 514/538; 514/617; 514/729; 514/739; 514/919; 523/122

(58) Field of Classification Search ........ 424/DIG. 10, 424/45, 47, 59, 60, 405–407, 78.03, 400, 424/401, 409, 78.37, 750, 720, 707; 574/919; 514/574, 919, 531, 315, 538, 551, 617, 738, 514/729, 739
See application file for complete search history.

(56) References Cited

U.S. PATENT DOCUMENTS

| | | | |
|---|---|---|---|
| 4,047,505 A | 9/1977 | McAndless | |
| 4,913,897 A | 4/1990 | Chvapil et al. | |
| 4,981,689 A | 1/1991 | Shikiname et al. | |
| 5,102,662 A | 4/1992 | Gallagher | |
| 5,143,900 A | 9/1992 | Steltenkamp et al. | |
| 5,196,200 A | 3/1993 | Wilson et al. | |
| 5,401,870 A | 3/1995 | Raleigh et al. | |
| 5,855,903 A | 1/1999 | Warren et al. | |
| 5,911,980 A | 6/1999 | Samour et al. | |
| 5,916,541 A | 6/1999 | Stewart | |
| 5,932,194 A | 8/1999 | Plessix et al. | |
| 6,203,812 B1 | 3/2001 | Ehrhard et al. | |
| 6,719,959 B1 * | 4/2004 | Gonzalez et al. | 424/45 |
| 2003/0044364 A1 * | 3/2003 | Meyer et al. | 424/59 |

* cited by examiner

Primary Examiner—Neil S. Levy
(74) Attorney, Agent, or Firm—Ohlandt, Greeley, Ruggiero & Perle, L.L.P.

(57) ABSTRACT

Disclosed is an insect repellent composition. The composition has an amount of an insect repellent active effective to repel insects when the composition is applied to the skin, and an amount of a urethane polymer sufficient to form a film on the surface of the skin. The composition also has a cosmetically-acceptable vehicle. Also disclosed is a method of repelling insects from the skin by applying the composition to the skin.

26 Claims, 4 Drawing Sheets

EXTENDED DURATION INSECT REPELLENT COMPOSITION AND METHOD OF APPLICATION TO THE SKIN

RELATED APPLICATIONS

This application claims priority from U.S. patent application Ser. No. 09/724,160 filed on Nov. 28, 2000 and PCT Patent Application Serial No. PCT/US01/44299 filed on Nov. 27, 2001.

BACKGROUND OF THE INVENTION

1. Field of the Invention

The present invention relates to an insect repellent composition. More particularly, the present invention relates to an insect repellent exhibiting extended duration of repellency on the skin. Further, the present invention relates to such a composition exhibiting water, sweat, and wear resistance. As used herein, the term "insect" is intended to mean any insect or arachnid.

2. Description of the Prior Art

Insect repellent compositions are available commercially in a variety of product forms, such as aerosol and pump sprays, creams, lotions and gels. Depending upon the product form, the compositions may be administered to both the skin and to clothing. The compositions may be administered in preparation for a variety of outdoor situations, such as picnicking, hiking, fishing, swimming and exercise.

A common problem associated with insect repellent compositions is a lack of duration of repellency. This translates into insufficient repellency and the need to re-apply often. Insect repellent compositions may wash off from exposure to water, sweating and/or physical contact with the skin.

It would be desirable to increase the duration of repellency of insect repellent compositions on the skin. It would further be desirable to have insect repellent compositions that resist removal by exposure to water, sweating and physical contact.

U.S. Pat. No. 4,913,897 to Chvapil et al. is directed to hydrogel compositions that form films on the surface of the skin to protect it against exposure to toxic substances and infections. This patent provides that such films may also contain an insect repellent. The urethane polymers of the present invention are not hydrogels nor do they form hydrogels in the present invention.

SUMMARY OF THE INVENTION

It is an object of the present invention to provide an insect repellent composition exhibiting extended duration and enhanced degree of repellency on the skin.

It is another object of the present invention to provide such a composition that provides even application and is water, sweat, and wear resistant.

It is a further object of the present invention to provide such a composition that is aesthetically acceptable.

These and other objects of the present invention are achieved by an insect repellent composition having an amount of an insect repellent active sufficient to repel insects when the composition is applied to the skin. The composition also has an amount of urethane polymer sufficient to form a thin, substantially continuous film on the skin. The composition also has a cosmetically acceptable vehicle.

Further according to the present invention, there is provided a method of repelling insects from the skin. The composition described above is applied to the skin. A thin urethane film, that is different from a hydrogel film, remains on the skin to enhance the function and effectiveness of the insect repellent. This urethane film is substantially uniform and provides superior coverage over the peaks and valleys of the skin surface, allowing for reduction of unprotected skin areas.

DETAILED DESCRIPTION OF THE INVENTION

Figure 1:
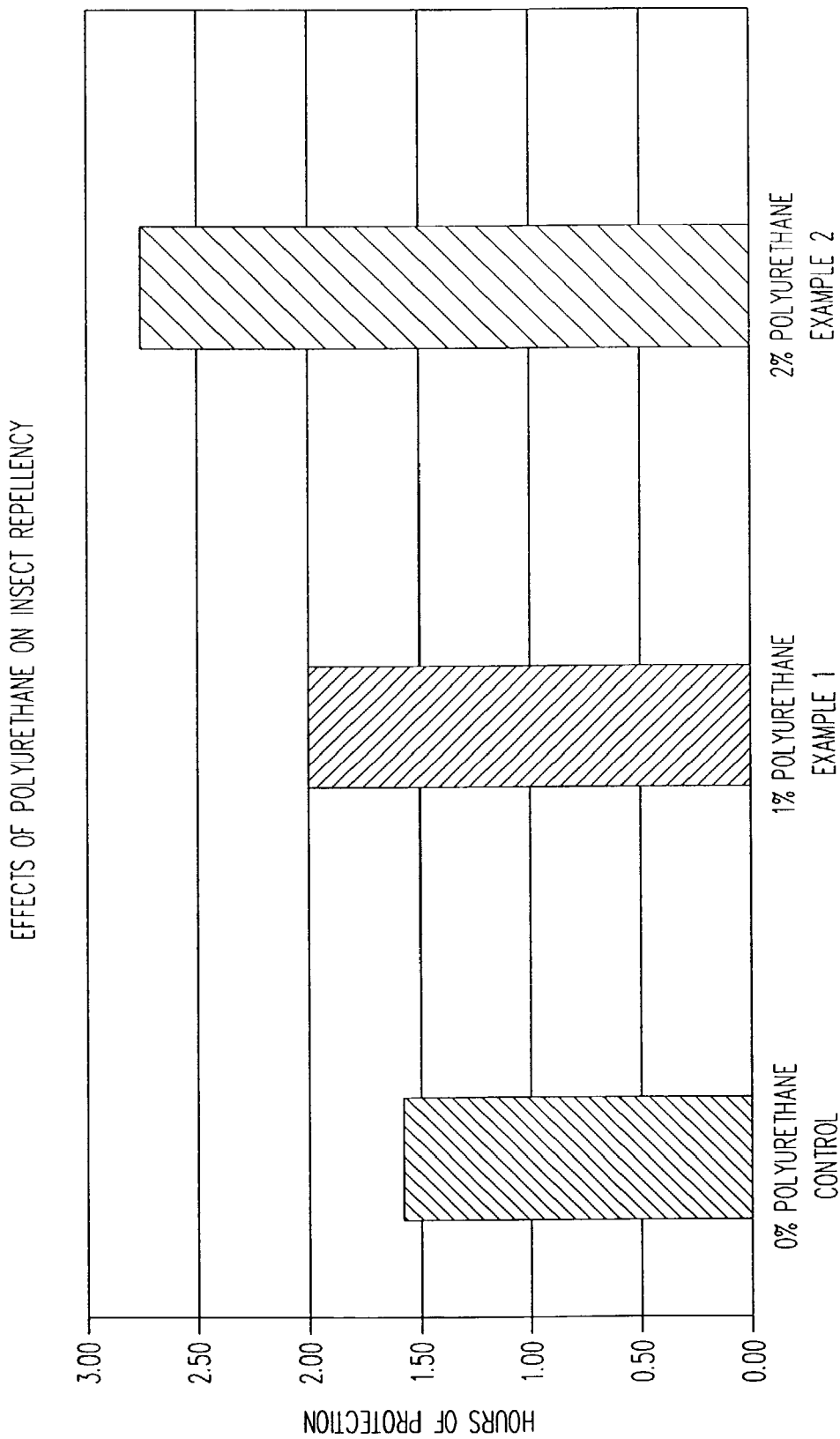
FIG. 1 is a bar graph illustrating the duration of insect repellency with varying levels of urethane polymers.

The present invention surprisingly found that an insect repellent composition can be produced that exhibits extended duration of repellency on the skin, and also enhanced insect repellency. In addition, the composition has superior spread characteristics on the skin. The composition may also exhibit water, sweat and wear resistance.

The composition can be formulated to be substantially transparent or otherwise aesthetically acceptable to impart a pleasant feel or sensation to the skin.

When applied to the skin, the present composition leaves a uniform film on the surface of the skin. The composition, which exhibits superior spread characteristics, provides more uniform and consistent coverage on the skin. The film has been found to maintain the duration of the insect repellent active(s) for a longer period of time than it would otherwise remain without the urethane polymer. The film also affords sustained release of the active. Additionally, enhanced resistance to water, sweat, and wear may be observed. In view of the foregoing advantages, the film has an enhanced degree of insect repellency for a given amount of insect repellent active employed. Thus, the amount of insect repellent active applied to the skin can be minimized.

The film-forming component of the present composition is a urethane polymer resin. Urethane polymers are formed by reactions of diisocyanate and glycol monomers. Preferred urethane polymer resins for use in the present invention are of the following formula:

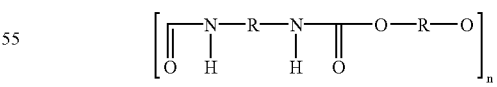

wherein R and R' are, independently, any linear or branched alkyl, alkylene, aliphatic or aromatic group having from 1 to about 30 carbon atoms, preferably about 6 to about 24 carbon atoms, and n is an integer from 2 to about 1000. When R' is cyclic, it preferably contains 6 or more carbon atoms. Urethane polymer resins useful in the present invention can be either hydrophobic or hydrophilic.

The most preferred urethane polymer resins are those referred to in the art as Polyurethane-1, Polyurethane-2, Polyurethane-4, Polyurethane-5 or mixtures thereof. These urethane polymer resins are described in the International Cosmetic Ingredient Dictionary and Handbook, 8$^{th}$ edition, Printed Edition Pages 1152–1153, which is incorporated herein by reference.

The urethane polymer is present in an amount about 0.1 wt. % to about 20 wt. % based on the total weight of the composition. The amount of the urethane polymer is preferably about 0.5 wt. % to about 10 wt. %, and, most preferably, about 1 wt. % to about 5 wt. %, based on the total weight of the composition.

The insect repellent or insect repellent active employed in the present composition may be any known in the art. Such actives that can be used in the present invention include, but are not limited to, N,N diethyl-m-toluamide (DEET), ethyl butylacetylaminopropionate (IR3535 by Merck Co.), hydroxy-ethyl isobutyl piperidine carboxylate (1-piperidinecarboxylic acid) (Bayer KBR 3023), oil of citronella, soy bean oil, lemon grass oil, geranium/geraniol oil, p-menthane-3,8-diol, or mixtures thereof. Other actives that can be used in the present invention are disclosed in U.S. Pat. Nos. 5,130,136 and 5,698,209, which are incorporated herein by reference.

The amount of insect repellent active is about 0.1 wt. % to about 70 wt. % based on the total weight of the composition. The amount of insect repellent active is preferably about 0.1 wt. % to about 25 wt. %, and, most preferably, about 5 wt. % to about 25 wt. %, based on the total weight of the composition.

The present composition may take any form known in the art. Such forms include, but are not limited to, a cream, lotion, gel, solution, ointment, towelette, mousse, stick, or pump spray or aerosol. If an aerosol spray, the composition may contain propellents, such as hydrocarbons, hydrofluorocarbons, chlorofluorocarbons and ethers. The composition may be aqueous or anhydrous. The composition may further be in an emulsion form.

The present composition preferably has a vehicle. Such vehicles may be any known in the art including, for example, water; vegetable oils; esters such as octyl palmitate, isopropyl myristate and isopropyl palmitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as cyclomethicone, dimethicone, dimethicone cross-polymers, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; and mixtures of the foregoing.

The vehicle is about 0.1 wt. % to about 99.8 wt. % of the total weight of the composition. Preferably, the vehicle is about 10 wt. % to about 93 wt. % of the total weight of the composition.

Optionally, the present composition may further include a sunscreen. The sunscreen may be any sunscreen know in the art. Such sunscreens include, but are not limited to, oxybenzone, sulisobenzone, dioxybenzone, menthyl antranilate, para aminobenzoic acid (PABA), dea methoxycinnamate, octyl methoxycinnamate, octocrylene, drometrizole trisiloxane, octyl salicylate, homomenthyl salicylate, octyl dimethyl PABA, TEA (triethanolamine) salicylate, titanium dioxide, zinc oxide, butylmethoxy dibenzoylmethane, methyl benzilidene camphor, octyl triazone, terephthalydiene, dicamphor sulfonic acid, ethyl PABA, hydroxy methylphenyl benzotriazole, methylene bis-benzotriazoyltetramethylbutylphenol (MBBT), bis-ethylhexyl oxyphenol) methoxyphenol triazine (BEMT), and mixtures thereof. Other sunscreens include those disclosed in U.S. Pat. No. 5,000,937, which is incorporated herein.

The sunscreen is preferably about 1 wt. % to about 45 wt. % of the total weight of the composition. Preferably, the sunscreen is about 2 wt. % to about 35 wt. % of the total weight of the composition. Most preferably, the sunscreen protects against both UVA and UVB radiation, and provides a SPF factor of at least about 2 and more preferably at least about 4. The preferred range of SPF protection is about 10 to about 50 and most preferably about 15 to about 30.

Further optionally, the present composition may have one or more of the following additional ingredients: anesthetics, anti-allergenics, antifungals, anti-inflammatories, antiseptics, chelating agents, colorants, depigmenting agents, emollients, emulsifiers, exfollients, fragrances, humectants, lubricants, moisturizers, pharmaceutical agents, preservatives, skin penetration enhancers, stabilizers, surfactants, thickeners, viscosity modifiers, vitamins or any combinations of these ingredients.

EXAMPLES 1 AND 2 AND CONTROL

Two compositions of the present invention were tested for duration of insect repellency. A control composition ("the Control") was likewise tested.

The compositions of Examples 1 and 2 had polyurethane concentrations of 1.0 wt. % and 2.0 wt. %, respectively, based upon the total weight of the compositions. The Control did not have any polyurethane (zero wt. %). The polyurethane resin employed was Polyurethane-1. All the compositions had 20 wt. % of IR3535 (Merck) as an insect repellent active, and q.s. with a mixture of alcohol and water.

The duration of insect repellency was tested on five subjects in a cage test utilizing a 1 cubic meter cage containing 200 mosquitoes.

The results are set forth in FIG. 1. The inclusion of polyurethane significantly increased the duration of repellency at both the 1.0 wt. % and 2.0 wt. % levels.

Optical Profilometry of Polymer Films

Figure 2:
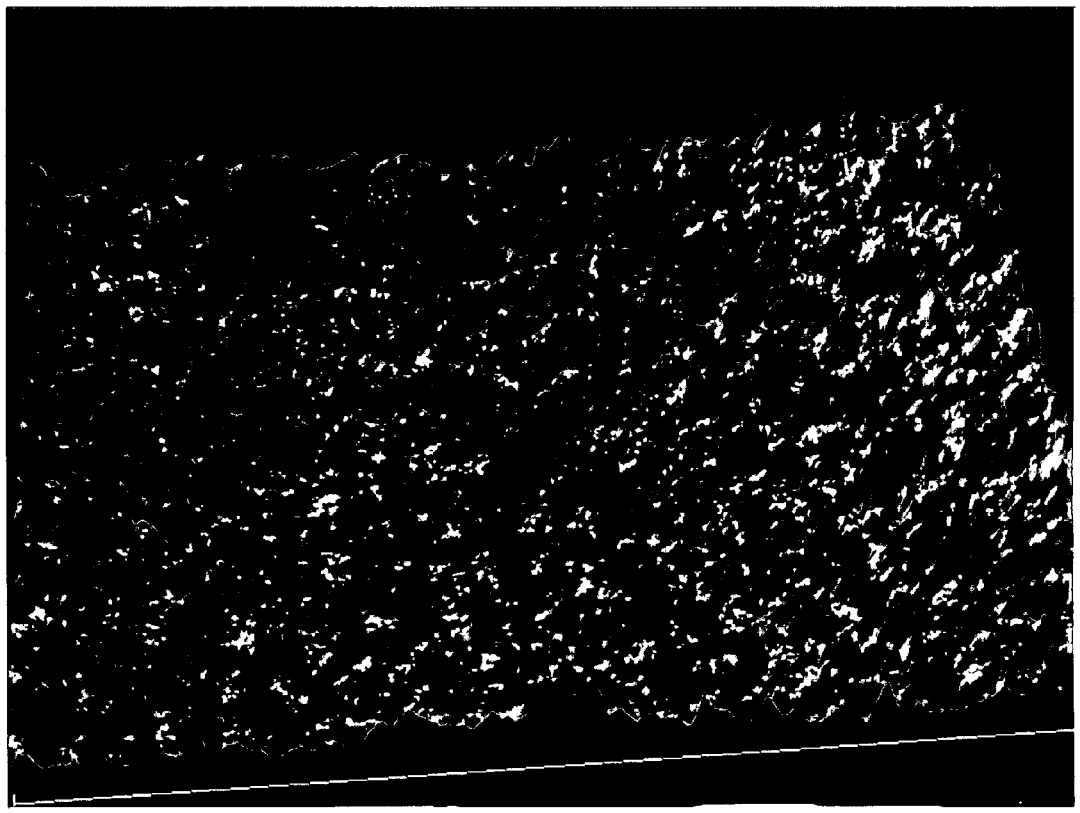
FIG. 2 is a view of a photograph of showing the topography of an artificial skin substrate without the application of the present invention.
Figure 3:
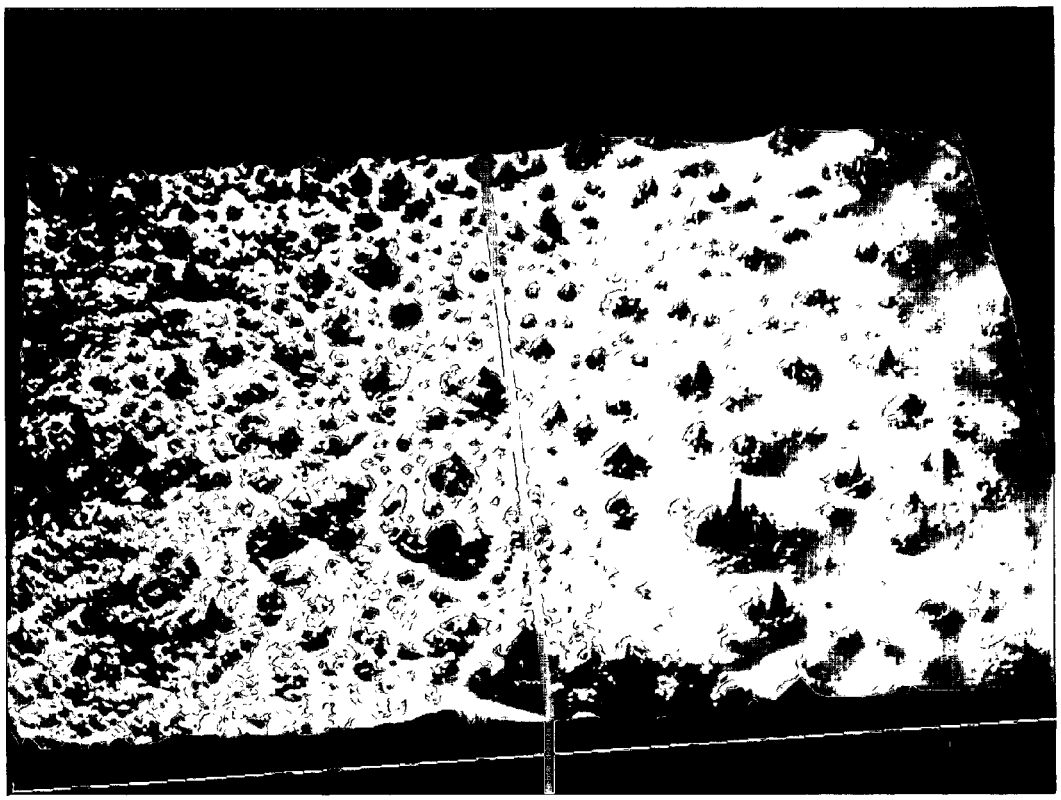
FIG. 3 is a view of a photograph showing the topography of a skin substrate with and without the application of an acrylic polymer not of the present invention.
Figure 4:
FIG. 4 is a view of a photograph showing the appearance of a skin substrate with and without the application of the present invention.

To determine the attributes of the present invention, an optical profilometry study of the present invention was performed on samples of an artificial skin substrate. FIG. 2 shows a 3-dimensional interactive display of the bare substrate as viewed under an optical profiler microscope. The peaks and valleys of the skin surface are clearly pronounced. As a comparison, tape was placed over the left side of a substrate sample. An insect repellent composition containing a conventional acrylic film forming polymer was applied to the right side of the substrate, allowed to dry and the tape was removed. A digital image was taken of this substrate surface using a Wyko NT1000 Optical Profiler made by Vecco. As is evident in FIG. 3, there was bleeding of the insect repellent composition under the tape, as well as non-uniform coverage of the peaks and valleys over which it was applied. As a further comparison, similar insect repellent composition having the urethane polymer film former of the present invention was prepared. Tape was placed over the left side of a substrate sample, and the inventive composition was applied to the right side and allowed to dry. The tape was removed and a digital image was taken of the substrate surface. As is evident from FIG. 4, this composition stayed where applied and did not run under the tape. Moreover, there was maximum, substantially uniform coverage of the peaks and valleys over which it was applied.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An insect repellent composition, comprising:
   an amount of an insect repellent active effective to repel insects when the composition is applied to skin; and
   an amount of a urethane polymer sufficient to form a film on the surface of the skin, wherein the urethane polymer has the following formula:

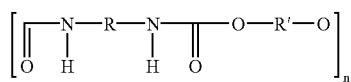

wherein R is any linear or branched alkyl, alkylene, aliphatic, cyclic, or aromatic group having from 1 to about 30 carbon atoms, wherein R' is any linear or branched alkyl, alkylene, aliphatic, cyclic or aromatic group having from 6 to about 30 carbon atoms, and wherein n is an integer from 2 to about 1000.

2. The composition of claim 1, further comprising a cosmetically-acceptable vehicle.

3. The composition of claim 1, wherein R' has 6 to about 24 carbon atoms.

4. The composition of claim 1, wherein R' is cyclic.

5. The composition of claim 1, wherein the urethane polymer is about 0.1 wt. % to about 20 wt. % based on the total weight of the composition.

6. The composition of claim 1, wherein the urethane polymer is about 0.5 wt. % to about 10 wt. % based on the total weight of the composition.

7. The composition of claim 1, wherein the amount of insect repellent active is about 0.1 wt. % to about 70 wt. % based on the total weight of the composition.

8. The composition of claim 1, wherein the urethane polymer does not form a hydrogel or a hydrogel film.

9. The composition of claim 1, wherein the insect repellent active is selected from the group consisting of N,N diethyl-m-toluamide, ethyl butylacetylaminopropionate, hydroxy-ethyl isobutyl piperidine carboxylate, oil of citronella, soy bean oil, lemon grass oil, geranium/geraniol oil, p-menthane-3,8-diol, and mixtures thereof.

10. The composition of claim 1, wherein the composition is in the form selected from the group consisting of a cream, lotion, gel, solution, towelette, mousse, stick, ointment, spray, and aerosol.

11. The composition of claim 1, further comprising a sunscreen.

12. The composition of claim 11, wherein the sunscreen is selected from a group consisting of oxybenzone, sulisobenzone, dioxybenzone, menthyl anthranilate, para aminobenzoic acid (PABA), octyl methoxycinnamate, octocrylene, drometrizole trisiloxane, octyl salicylate, homomenthyl salicylate, octyl dimethyl PABA, triethanolamine salicylate, titanium dioxide, zinc oxide, butylmethoxy dibenzoylmethane, methyl benzilidene camphor, octyl triazone, terephthalydiene dicamphor, sulfonic acid, ethyl PABA, hydroxy methylphenyl benzotriazole, methylene bis-benzotriazoyltetramethylbutylphenol, bis-octyloxyphenol methoxyphenol triazine, and mixtures thereof.

13. The composition of claim 12, wherein the sunscreen is selected from a group consisting of oxybenzone, octyl methoxycinnamate, octocrylene, octyl salicylate, titanium dioxide, zinc oxide, butylmethoxy dibenzoylmethane, methylene bis-benzotriazoyltetramethylbutylphenol, bis-octyloxyphenol methoxyphenol triazine, and mixtures thereof.

14. An insect repellent composition, comprising:
   an amount of an insect repellent active effective to repel insects when the composition is applied to skin;
   about 0.1 wt. % to about 20 wt. % based on the total weight of the composition of a urethane polymer, wherein the urethane polymer forms a film on the surface of the skin, wherein the urethane polymer has the following formula:

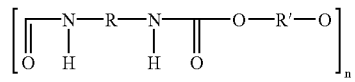

wherein R is any linear or branched alkyl, alkylene, aliphatic, cyclic, or aromatic group having from 1 to about 30 carbon atoms, wherein R' is any linear or branched alkyl, alkylene, aliphatic, cyclic or aromatic group having from 6 to about 30 carbon atoms, and wherein n is an integer from 2 to about 1000; and
   a cosmetically-acceptable vehicle.

15. The composition of claim 14, wherein R' is cyclic.

16. The composition of claim 14, wherein R' has 6 to about 24 carbon atoms.

17. An insect repellent composition comprising:
   an effective amount of an insect repellent;
   a film-forming urethane polymer; and
   a volatile component,
   wherein the composition is dispensed from a spray container, wherein the urethane polymer has the following formula:

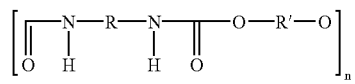

wherein R is any linear or branched alkyl, alkylene, aliphatic, cyclic, or aromatic group having from 1 to about 30 carbon atoms, wherein R' is any linear or branched alkyl, alkylene, aliphatic, cyclic or aromatic group having from 6 to about 30 carbon atoms, and wherein n is an integer from 2 to about 1000.

18. The composition of claim 17, wherein the composition is substantially anhydrous.

19. The composition of claim 17, wherein the spray container is selected from the group consisting of a pump spray container and an aerosol spray container.

20. The composition of claim 17, wherein the volatile component is selected from the group consisting of one or more alcohols, hydrocarbons, ethers, silicones, water, and mixtures thereof.

21. The composition of claim 17, wherein R' has 6 to about 24 carbon atoms.

22. A method of repelling insects from the skin, comprising applying to the skin the composition of claim 1.

23. The method of claim 22, wherein the urethane polymer is about 0.1 wt. % to about 20 wt. % based on the total weight of the composition.

24. The method of claim 22, wherein R' is cyclic.

25. The method of claim 22, wherein the insect repellent active is about 0.1 wt. % to about 70 wt. % based on the total weight of the composition.

26. The composition of claim 22, wherein R' has 6 to about 24 carbon atoms.

* * * * *